(12) United States Patent
Sonnenschein et al.

(10) Patent No.: US 7,959,052 B2
(45) Date of Patent: Jun. 14, 2011

(54) ENDOSCOPIC STAPLER HAVING CAMERA

(75) Inventors: Elazar Sonnenschein, Beer Sheva (IL); Amir Govrin, Tel Aviv (IL)

(73) Assignee: Medigus Ltd., Omer (IE)

( * ) Notice: Subject to any disclaimer, the term of this patent is extended or adjusted under 35 U.S.C. 154(b) by 230 days.

(21) Appl. No.: 12/301,058

(22) PCT Filed: May 31, 2007

(86) PCT No.: PCT/IL2007/000659
§ 371 (c)(1),
(2), (4) Date: Nov. 26, 2008

(87) PCT Pub. No.: WO2007/141776
PCT Pub. Date: Dec. 13, 2007

(65) Prior Publication Data
US 2009/0250501 A1    Oct. 8, 2009

(30) Foreign Application Priority Data

Jun. 5, 2006  (IL) .......................................... 176133

(51) Int. Cl.
*A61B 17/064* (2006.01)
(52) U.S. Cl. ............... 227/176.1; 227/175.1; 227/175.3; 227/19; 227/120; 227/147; 128/898; 606/139; 606/219
(58) Field of Classification Search ............... 227/175.1, 227/175.3, 176.1, 19, 120, 132–13, 147; 128/898; 606/139, 219
See application file for complete search history.

(56) References Cited

U.S. PATENT DOCUMENTS

| 2,632,889 | A | * | 3/1953 | Beecroft ....................... 227/120 |
| 3,583,622 | A | * | 6/1971 | Graeff .......................... 227/120 |
| 5,389,098 | A |   | 2/1995 | Tsuruta et al. |
| 5,395,030 | A | * | 3/1995 | Kuramoto et al. ......... 227/179.1 |
| 5,503,320 | A | * | 4/1996 | Webster et al. ............ 227/176.1 |

(Continued)

FOREIGN PATENT DOCUMENTS

WO  WO 00/53102  9/2000

(Continued)

OTHER PUBLICATIONS

International Preliminary Report on Patentability for PCT/IL2007/000659; mailed Feb. 24, 2009 -4 pages.

*Primary Examiner* — Rinaldi I. Rada
*Assistant Examiner* — Michelle Lopez
(74) *Attorney, Agent, or Firm* — Roach Brown McCarthy & Gruber, P.C.; Kevin D. McCarthy

(57) ABSTRACT

The invention is a stapler device comprising an anvil and staple cartridge located in the distal tip of an endoscopic device. The staple cartridge is comprised of a fixed proximal portion and a moveable distal portion, which slides into said fixed portion. Means are provided for moving the anvil back and forth, such that the anvil pushes against the distal face of the staple cartridge thereby pushing the moveable portion of the staple cartridge into the fixed portion and causing the staples to be ejected from said staple cartridge passively without said staples moving. The stapler of the invention has two embodiments, a side fastening embodiment and a front fastening embodiment. The endoscopic device that comprises the stapler can be used to perform many different stapling tasks, e.g. closure of a hole in the wall of an internal organ.

14 Claims, 15 Drawing Sheets

U.S. PATENT DOCUMENTS

| | | | |
|---|---|---|---|
| 5,620,452 A | 4/1997 | Yoon | |
| 5,651,491 A | 7/1997 | Heaton et al. | |
| 5,662,260 A | 9/1997 | Yoon | |
| 5,676,674 A | 10/1997 | Bolanos et al. | |
| 5,772,099 A | 6/1998 | Gravener | |
| 5,868,760 A * | 2/1999 | McGuckin, Jr. | 606/139 |
| 5,957,363 A | 9/1999 | Heck | |
| 6,119,913 A * | 9/2000 | Adams et al. | 227/176.1 |
| D436,010 S | 1/2001 | Nakamura et al. | |
| 6,302,311 B1 | 10/2001 | Adams et al. | |
| 6,343,731 B1 | 2/2002 | Adams et al. | |
| 6,872,214 B2 | 3/2005 | Sonnenschein et al. | |
| 7,753,249 B2 * | 7/2010 | Sonnenschein et al. | 227/176.1 |

FOREIGN PATENT DOCUMENTS

| | | |
|---|---|---|
| WO | WO2005/002210 | 1/2005 |
| WO | WO2005/115221 | 12/2005 |

* cited by examiner

ENDOSCOPIC STAPLER HAVING CAMERA

CLAIM OF PRIORITY

This application claims priority as a 371 of international of PCT/IL2007/000659, filed on May 31, 2007; which claims priority to Israeli patent application number 176133, filed on Jun. 5, 2006.

FIELD OF THE INVENTION

The present invention is related to the field of staplers. Specifically the invention relates to the field of linear surgical staplers and endoscopic staplers.

BACKGROUND OF THE INVENTION

Linear surgical staplers are well known in the prior art. Typical examples of such devices are described in WO 00/53102, U.S. Pat. No. 5,772,099, U.S. Pat. No. 5,676,674, U.S. Pat. No. 5,389,098, and U.S. Pat. No. 6,872,214. All of these devices comprise a staple cartridge in which is stored one or more arrays of staples. The essentially U-shaped staples are stored with their legs aligned with and pointing in the direction of slots in the face of the cartridge. The staples actively forced to move through the slots when the firing mechanism is activated. The firing mechanism comprises some form of sliding cam or wedge positioned so that it can be moved longitudinally under the staples. When caused to move the wedge slides under the staple and either directly or with the aid of a staple pusher forces the staple to move in the direction of the slot until the staple is eventually forced completely out of the cartridge. The mechanical arrangement of the cams, etc. is of varying degrees of complexity, but in all cases is not simple and requires complex manufacturing and assembly methods and unnecessary expense all of which could be reduced if a simpler stapler firing method could be devised.

A frequent surgical procedure that has to be performed by surgeons is the closure of holes that exist in biological tissue. These holes can be either the result of injury or created by the surgeon to gain access to internal parts of the body on which he must operate.

Traditional methods of closure of the holes are stitching using a needle and natural or artificial thread, gluing the edges of the hole together, or fastening with one of many different forms of surgical fastener of staple. A hole on the outer surface of the body, e.g. a bullet hole or an incision cut into the outer surface of the abdominal wall for insertion of a laparoscope, is visible, easy to access, and easy to close. When the hole is in the wall of an internal organ, e.g. the wall of the stomach, the closure is much more complex. In this case, either major surgery is performed to open the body and gain access to the site of the hole, or laparoscopic or endoscopic devices and techniques can be employed. To perform the closure procedure laparoscopically or endoscopically there must be provided visualization means in order to be able to view the hole and control the operation of the various instruments used to close it, grabbing means to pull and hold the edges of the hole together, and fastening means to attach the edges of the tissue together thereby closing the hole. Introducing and manipulating the instruments and accessories into the body of the patient requires a great deal of skill and the cooperative action of a team of trained personnel.

It is a purpose of the present invention to provide an endoscopic stapler device that comprises a simpler mechanism for firing the staples from the cartridge than that which exists in the prior art.

It is another purpose of the present invention to provide an endoscopic stapler device that comprises all the features necessary for a surgeon to locate and close a hole in the tissue of an internal organ.

Further purposes and advantages of this invention will appear as the description proceeds.

SUMMARY OF THE INVENTION

In a first aspect the present invention is a stapler comprising an anvil and a staple cartridge containing an array of staples. The cartridge comprises portions a fixed proximal portion and a moveable distal portion. When a force pushing the distal portion in a proximal direction is applied to its distal face the distal portion slides into the fixed portion. The stapler also comprises means for moving the anvil back and forth in a direction parallel to an imaginary axis passing through the distal face of the staple cartridge and the face of the cartridge. The stapler may also comprise staple pushers or internal slots which act as a backstop to prevent the staples from moving in the proximal direction. The stapler is characterized in that the staples are ejected from the staple cartridge passively without the staples moving.

The staples are ejected from the staple cartridge passively without the staples moving by activating the means for moving the anvil to cause the anvil face to move proximally until it engages the distal cartridge face and causing the moveable distal portion of the cartridge to begin to be pushed into the fixed proximal portion of the anvil. This causes the legs of the staples to exit the cartridge through slots in the distal cartridge face, to penetrate the layers of material located between the faces of the anvil and the staple cartridge, and to curl in the corresponding depressions on the face of the anvil, thereby stapling the layers together.

A preferred embodiment of the stapler of the invention is an endoscopic surgical stapler for stapling tissue within a body cavity. The stapler is comprised of:
 (a) an endoscopic device comprising an insertion section ending in a distal tip;
 (b) a stapler of the invention;
 (c) tissue grasping means which can be advanced out of and retracted into channels that travel through the insertion section and exit the distal tip at a location between the proximal face of the anvil and the distal face of the cartridge; and
 (d) one or more visualization means enabling observation of the operating site and inspection of the results of the stapling procedure.

The endoscopic surgical stapler of the invention has two embodiments: The first in which the anvil, the cartridge, and the grasping means are located in a recess on the side of the distal tip and the second in which the anvil, the cartridge, and the grasping means are located on the front of the distal tip.

The insertion tube of the endoscopic surgical stapler can comprise: a flexible section followed by an articulation section, a semi rigid section, or a semi rigid section followed by an articulation section.

Some or all of the components of the endoscopic surgical stapler can be sterilizable and reusable. In some embodiments all components are discarded after a single procedure. The visualization means can be: a miniature CCD or CMOS camera, an objective lens optically coupled to proximally located processing and display means, or a bundle of imaging fibers. The tissue grasping means can be screws comprised of stiff wire bent into a spiral or forceps.

In another aspect the present invention is a method for operating the endoscopic surgical stapler to staple tissue within a body cavity. The method comprises the steps of:

(a) inserting the endoscope into the body cavity;
(b) using the visualization means to see when the tissue to be stapled is viewed in the correct position relative to the grasping means;
(c) using the grasping means to grab the edges of the tissue to be stapled together;
(d) pulling the grasping means with the tissue attached back into the channels;
(e) activating the means for moving the anvil causing the anvil to move towards the front face of the cartridge until the grabbed tissue is compressed between the faces of the anvil and the cartridge, whereupon, upon further motion of the anvil towards the cartridge, the legs of the staples begin to exit the slots, to penetrate the layers of the grabbed tissue and curl in the depressions;
(f) activating the grasping means to release their grip on the tissue;
(g) activating the anvil moving means causing the anvil to move back to its original position, thereby freeing the stapled tissue;
(h) inspecting the stapled tissue using the visualization means;
(i) and withdrawing the endoscopic device from the body cavity.

The tissue to be stapled may contain a hole which is closed by stapling. If the hole in the tissue is a large one, then one or more endoscopic surgical staplers of the invention may be inserted into the cavity sequentially to apply two or more arrays of staples next to each other until the hole is completely closed.

The endoscopic surgical stapler of the invention can be inserted into the body cavity through the working channel of a standard endoscope. In this case, the visualization means can be located on the standard endoscope and the stapler, without a camera and illumination fibers, is mounted on a flexible shaft that is inserted through the working channel of the standard endoscope.

All the above and other characteristics and advantages of the invention will be further understood through the following illustrative and non-limitative description of preferred embodiments thereof, with reference to the appended drawings. In the figures, components having like structure or like functions are designated by the same identification numeral.

DETAILED DESCRIPTION OF PREFERRED EMBODIMENTS

The stapler device of the invention comprises an anvil and staple cartridge located in the distal tip of an endoscopic device which can have either a rigid (i.e. laparoscope), semi-rigid, or flexible insertion section. According to a preferred embodiment of the invention the insertion tube of the endoscopic device comprises a proximal flexible section followed by an articulation section. The stapler of the invention has two embodiments, a side fastening embodiment and a front fastening embodiment. The endoscopic device that comprises the stapler can be used to perform many different stapling tasks, e.g. closure of a hole in the wall of an internal organ. The endoscopic device comprising the stapler of the invention can be either totally or partially sterilized after each use or, in some embodiments disposed after a single procedure has been performed.

Figure 11:
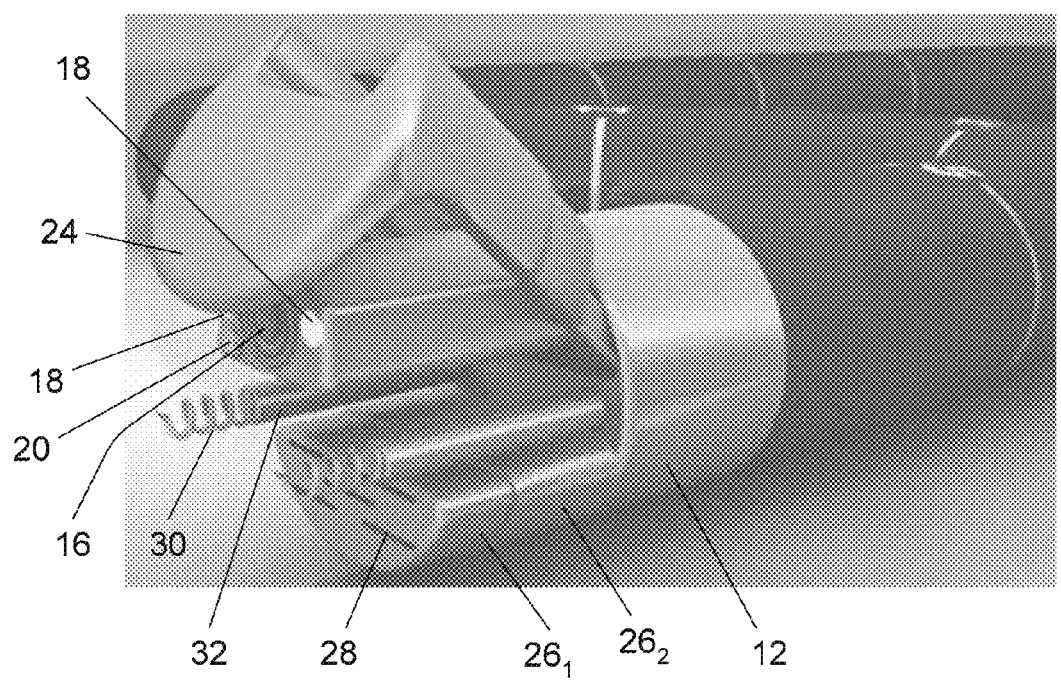
FIG. 11 to FIG. 13 show the front fastening embodiment of the stapler of the invention in the open and closed configurations.
Figure 12:
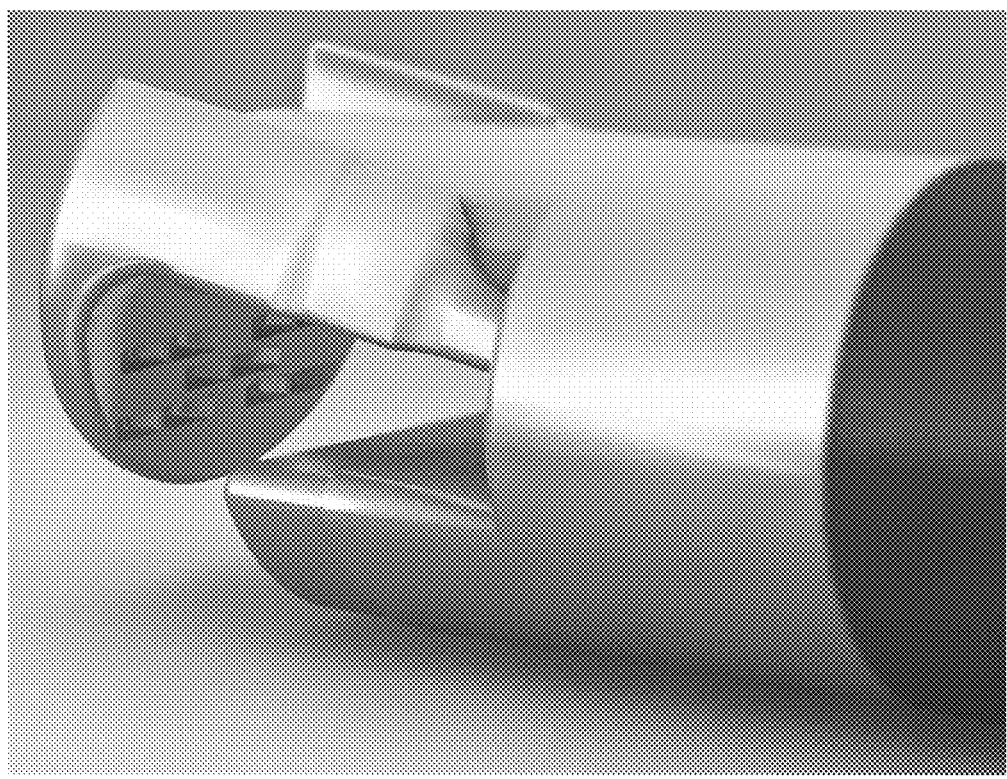
Figure 13:
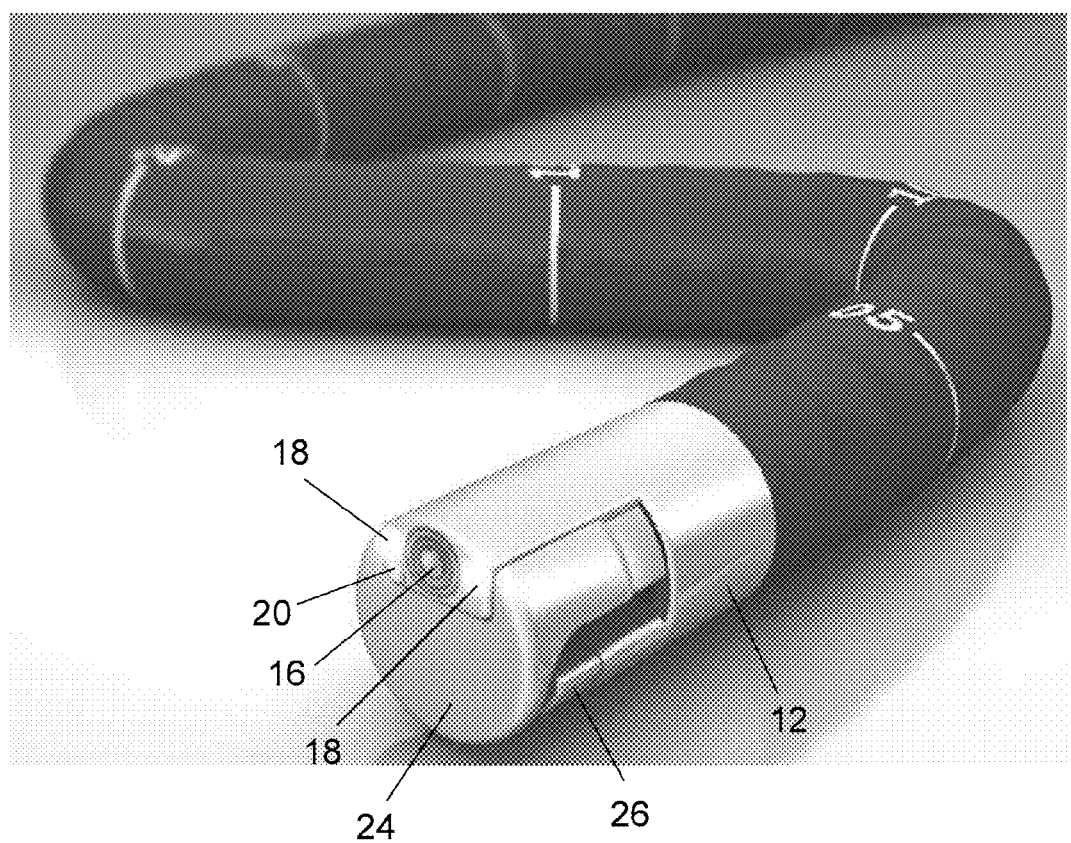

FIG. 1 to FIG. 8 and FIG. 10 show different views of the side fastening embodiment of the invention in order to assist in the description of the essential features of the stapler and its operation. FIGS. 9A to 9F schematically show different stages of the procedure of using the side fastening embodiment of the stapler device of the invention to close a hole in biological tissue. FIG. 11 to FIG. 13 show the front fastening embodiment of the stapler of the invention. FIGS. 14A to 14F schematically show different stages of the procedure of using the front fastening embodiment of the stapler device of the invention to close a hole in biological tissue.

Figure 1:
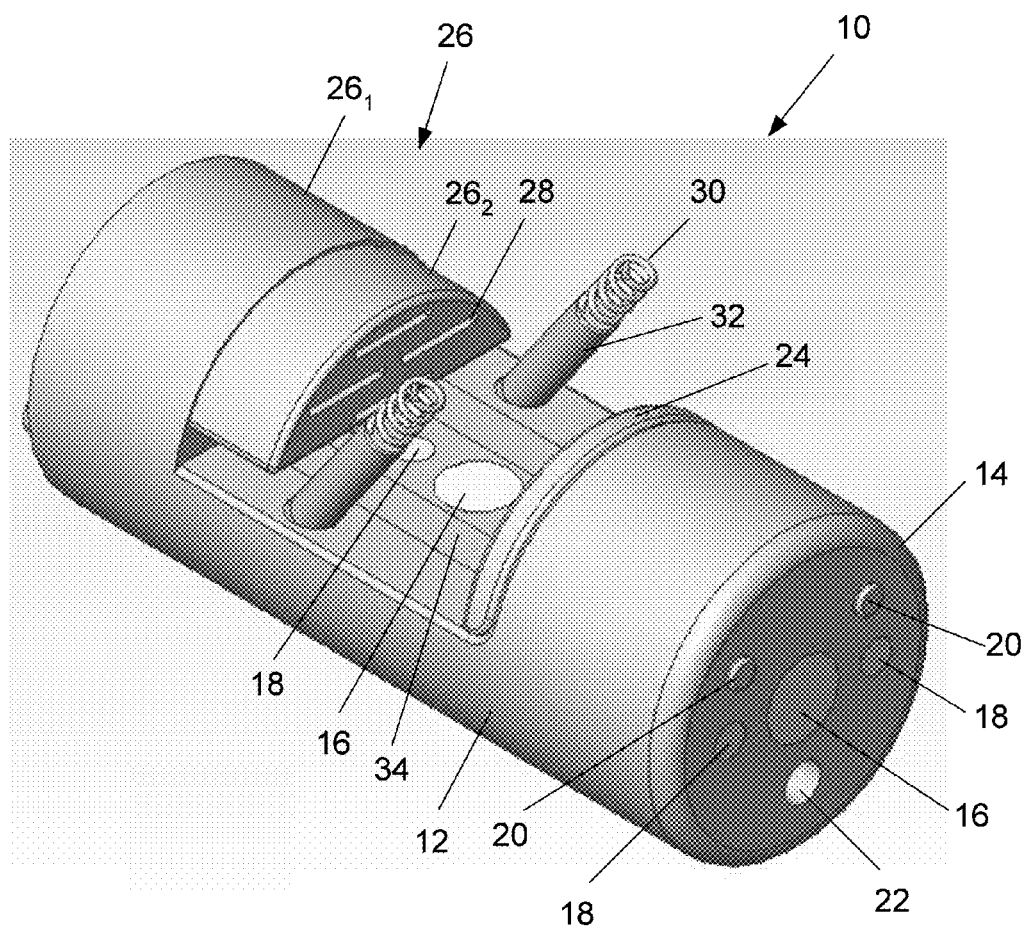
FIG. 1 to FIG. 3 are general views from above showing the side closing embodiment of the stapler of the invention located in the distal tip of an endoscope.
Figure 2:
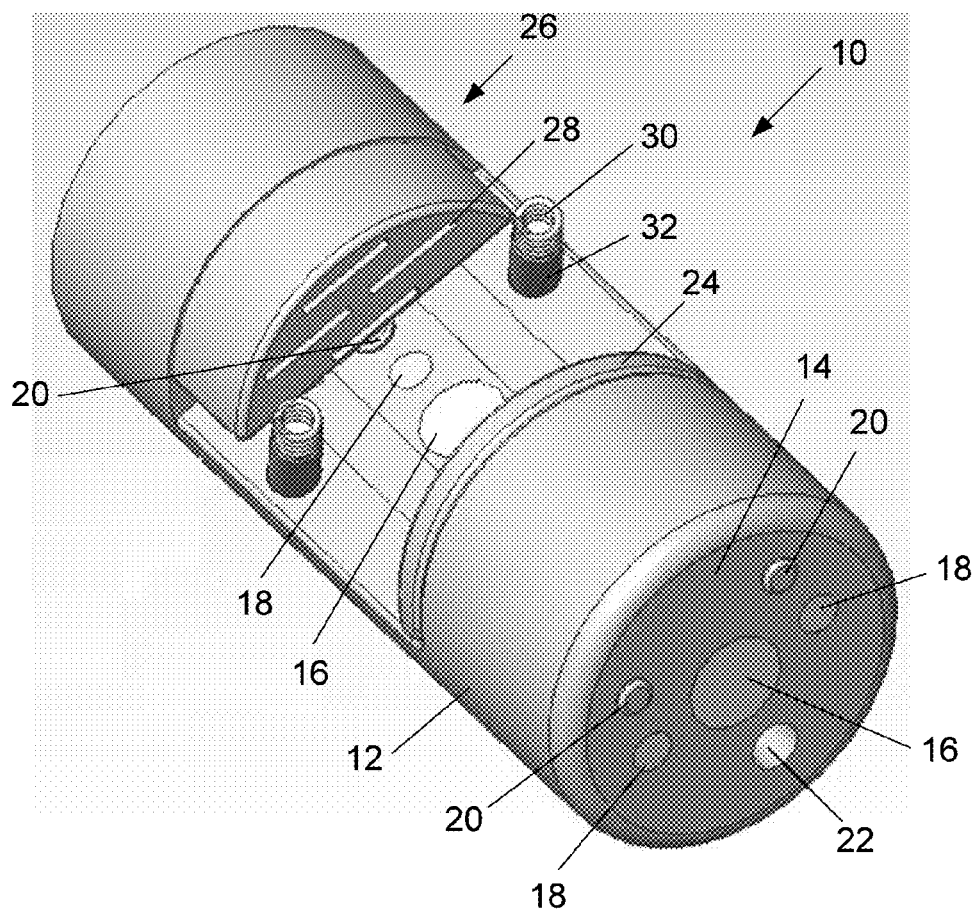
Figure 3:

FIG. 1 FIG. 3 are general views from above showing the side closing embodiment of the stapler 10 of the invention located in the distal tip 12 of an endoscope. On the distal face 14 can be seen a camera 16; the ends of two optic fibers 18, which provide light to illuminate the field of view of the camera; two nozzles 20 to spray air or water to keep the camera lens clean; and a working channel 22, which can be used to introduce other devices, e.g. ultrasound probe, forceps, etc. Experienced persons will recognize that the configuration and type of elements shown on the distal face in the figures is illustrative only, is not crucial to the present invention, and is related to the particular procedure to be performed and to the accessories provided. As a specific example, the camera 16, could be replaced with other viewing means such as an objective lens whose image is transferred by optical fibers to proximal processing and display means or by a bundle of imaging fibers.

An alternate configuration to that described above, i.e. stapler, camera, and illumination fibers in the same device, could comprise a standard endoscope that contains visualization means (e.g. camera or image fiber) with a working channel and advancing a stapler of the invention mounted on a flexible shaft without a camera and illumination fibers through the working channel of the standard endoscope that provides the image scene to the site of the tissue to be stapled.

Suitable cameras for use with the present invention are described in published international patent applications WO2005/002210 and WO2005/115221 by the same applicant, the descriptions of which, including publications referenced therein, are incorporated herein by reference. Cameras are based on CCD or CMOS technology can be manufactured at a cost that is low enough to allow them to be discarded after a single use.

Stapler 10 is comprised of two components: the anvil 24, which is an essentially vertical surface at the bottom of which are attached two horizontal legs 34, a staple cartridge 26, which contains an array of staples that exit through slots 28 when the stapler is activated as described hereinbelow. The stapler cartridge is composed of two sections: a proximal section $26_1$, which is either fixedly attached to or manufactured as an integral part of the distal tip, and a distal section $26_2$, which can be slid into proximal section $26_1$ by pushing on the distal face of section $26_2$. In the side closing embodiment of stapler 10 the cartridge 26 and anvil 24 are located at the proximal and distal ends respectively of a recess cut into the side of distal tip 10. On the floor of the recess are located a camera 16, one or more light fibers 18, and water or air nozzles 20 in order to visualize the hole and the tissue grasping procedure as well as to inspect the tissue after the staples are ejected from the cartridge. In order to grasp the tissue, there are provided grasping means. In the figure are shown two screws 30 comprised of stiff wire bent into a spiral shape, but other arrangements, e.g. grasping forceps could be used. The screws 30 pass through overtubes 32 located in channels through the insertion tube of the endoscope. They can be independently advanced, withdrawn, and rotated about their longitudinal axis from the handle at the proximal end of the endoscope.

Figure 4:
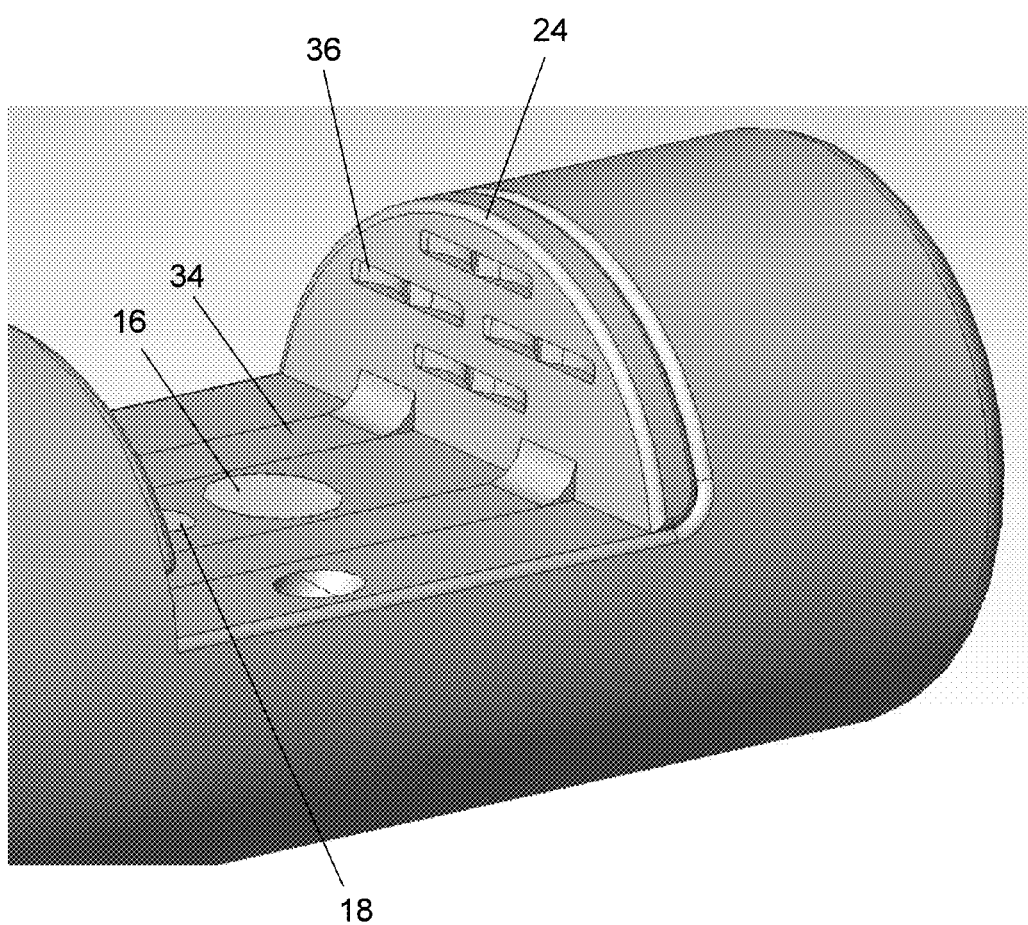
FIG. 4 is an enlarged view showing the anvil in the distal tip.
Figure 5:
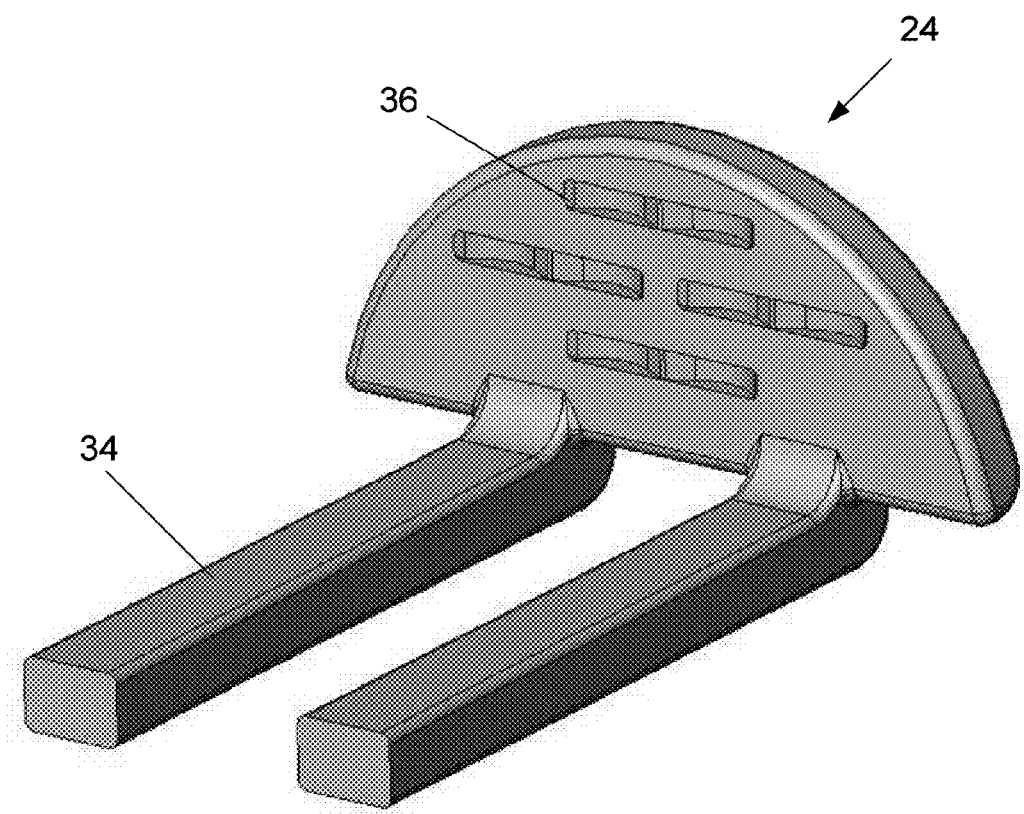
FIG. 5 shows the anvil removed from the endoscope.
Figure 7:
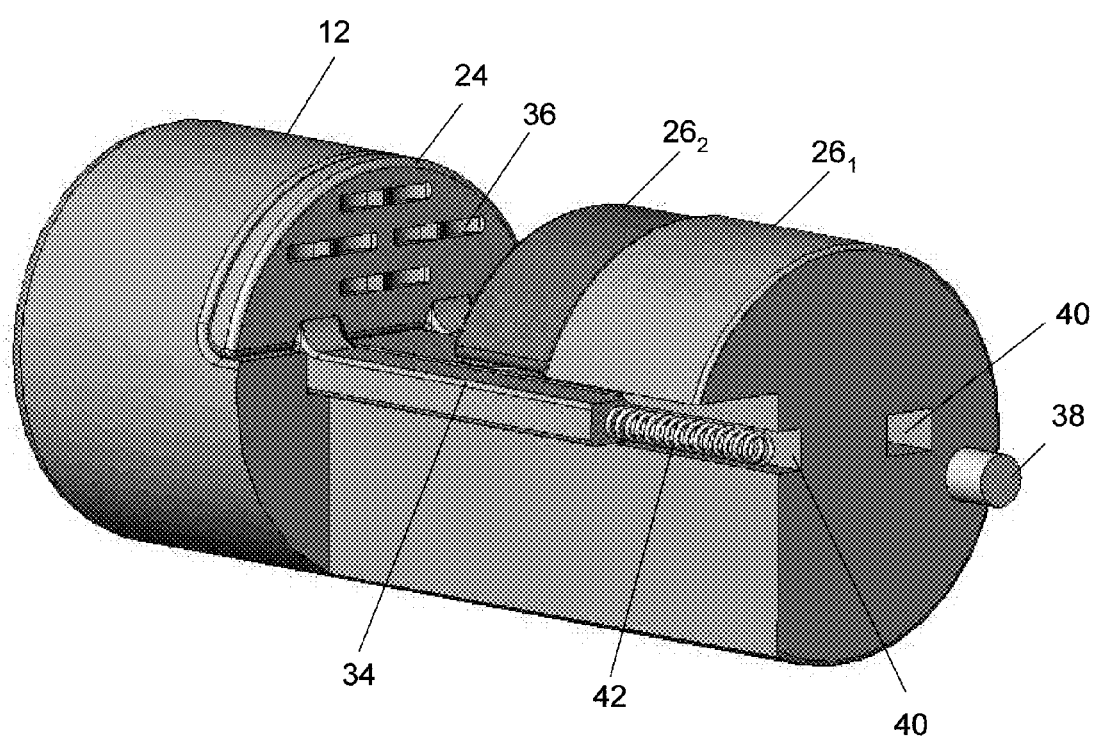

FIG. 4 is an enlarged view showing the anvil 24 in the distal tip. In the figure the depressions 36 into which the legs of the staples enter and are curled when the staples are ejected from the stapler are seen on the face of the anvil. The stapler can be designed to utilize different sizes of staples depending on the diameter of the endoscope and properties of the tissue to be fastened. Typical standard sizes that can be used are 2, 2.5, 3, 3.3, and 4.8 mm staples made from titanium, Stainless steel or biodegradable materials. In FIGS. 1-5, the diameter of the endoscope is 8-15 mm (depending of the number of staples) and the stapler comprises an array of four 4.8 mm staples. FIG. 7 shows the same endoscope to which is fitted a stapler comprising an array of eight 2 mm staples. Other configurations are contemplated, for example a 4 mm diameter endoscope that can be inserted through the 4.2 mm working channel of a standard flexible endoscope. FIG. 5 shows the anvil 24 removed from the endoscope.

Figure 6:
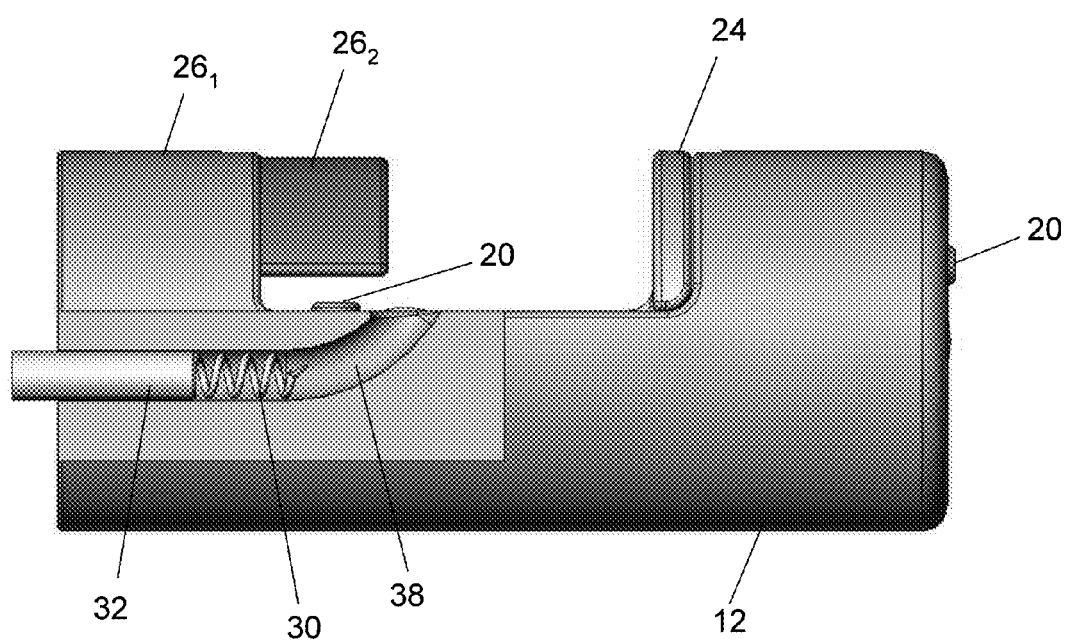
FIG. 6 and FIG. 7 are views with parts of the of the surface removed to reveal details of the interior of the distal tip.

FIG. 6 and FIG. 7 are views with parts of the surface removed to reveal details of the interior of the distal tip 12. In FIG. 6 can be seen the channel 38, through which the overtube 32 and enclosed screw 30 are advanced through the length of the endoscope. In FIG. 7 can be seen the channels 40 in which the legs 34 of the anvil can slide. Not shown in FIG. 7 is a cable that is attached to the proximal end of each leg 34, passes through the center of spring 42, and then passes through a channel in the insertion tube of the endoscope to the handle where its proximal end is attached to a mechanism that can be used to pull the entire anvil 24 in a proximal direction. When anvil 24 is pulled in a proximal direction, the proximal end of spring 42 butts up against a stopper (not shown) and is compressed. When the tension on the cable used to pull the anvil proximally is released, spring 42 pushes anvil 24 in the distal direction.

Figure 8:
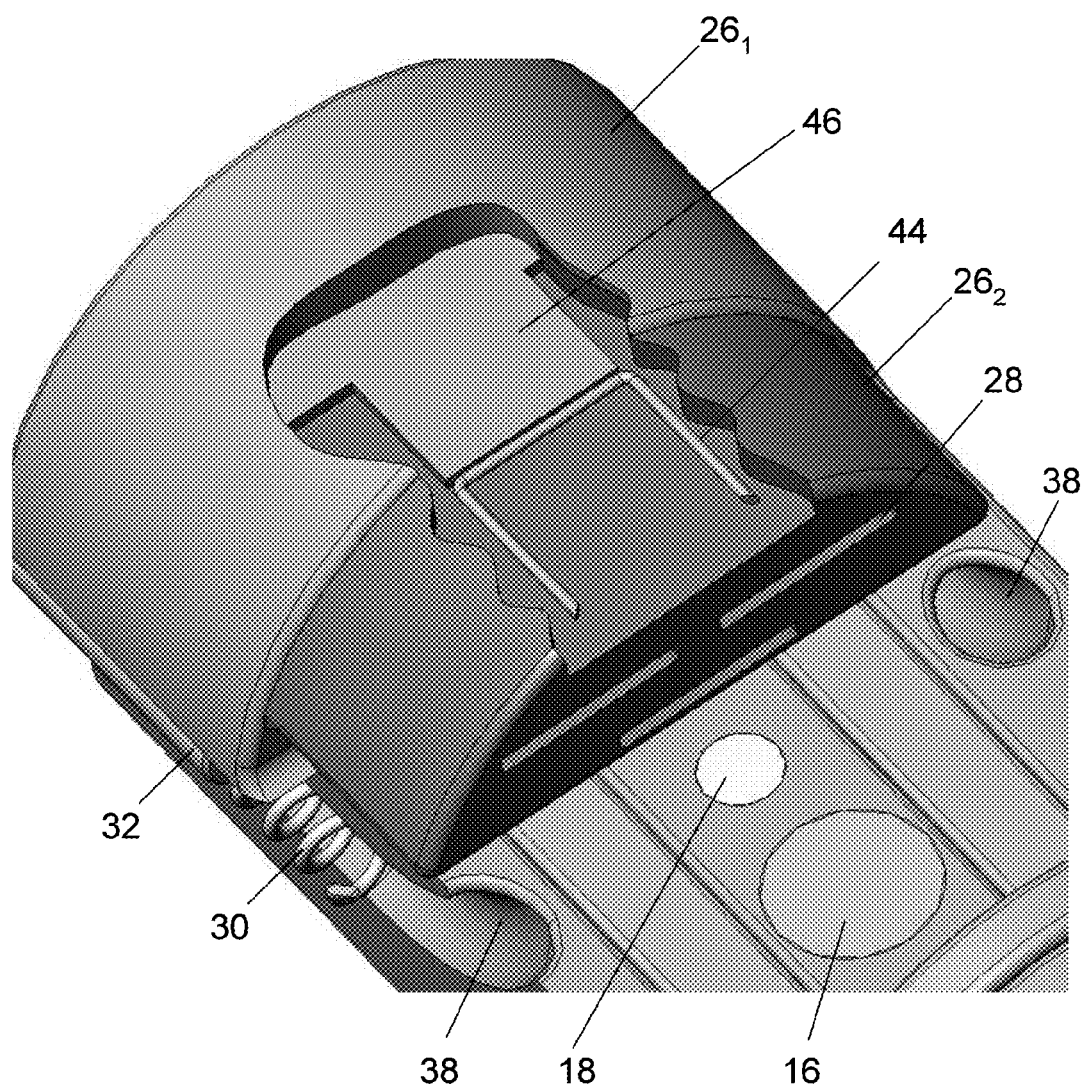
FIG. 8 is a view with part of the wall of the staple cartridge removed to reveal its interior.

FIG. 8 is a top view with part of the wall of the staple cartridge 26 removed to reveal its interior. The cartridge 26 of the stapler of the invention does not comprise any arrangement of cams to actively fire the staples. When the anvil 24 is pulled proximally as described herein above, the face of anvil 24 engages the face of cartridge 26 and pushes distal section $26_2$ proximally causing it to slide into proximal section $26_1$. In contrast to prior art staplers, neither the staple pushers 46 nor the staples 44 move. The staple pushers that are shown in the figure could be replaced by any other arrangement, e.g. internal slots, which act as a backstop to prevent staples 44 from moving in the proximal direction. In this way the legs of staples 44 are passively forced to exit the distal part $26_2$ of the cartridge through slots 28 and engage the matching depressions 36 on the face of anvil 34. Continued pulling on the cables attached to the legs 34 of the anvil 36 causes more and more of the length of the legs of staples 44 to exit through slots 28 and the legs of the staples start to curl. The process continues until the staples 44 completely exit the cartridge 26, the legs are completely curled and the stapling process is completed. The cartridge 26 may contain one or more springs to provide a gradually yielding counter force to that exerted by the anvil, thereby aiding to provide a smooth exit of the staples and, if necessary, to return distal section $26_2$ to its original position as the anvil moves in the distal direction. An arrangement such as a number of projections on the face of either the anvil or cartridge that would penetrate the tissue and leave a gap of the required distance between the two faces or internal springs can be provided if necessary to maintain an exact predetermined distance between anvil and cartridge faces to guarantee that the staple legs would curl correctly and also to prevent compression of the tissue that could cause irreversible damage.

Figure 9A:
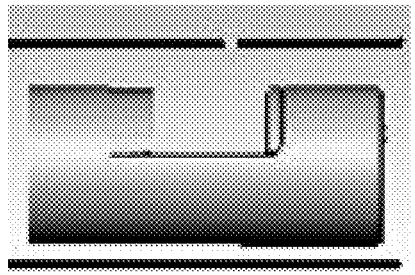
FIGS. 9A to 9F schematically show different stages in the operation of the side fastening embodiment of the stapler to close a hole in biological tissue.

FIGS. 9A to 9F schematically show different stages in the operation of the side fastening embodiment of the stapler to close a hole in biological tissue. The procedure is as follows:

FIG. 9A—The endoscope is inserted into the body cavity using the camera 16 on the distal face 14 for visualization until the hole in the tissue is viewed using the side facing camera 16.

Figure 9B:
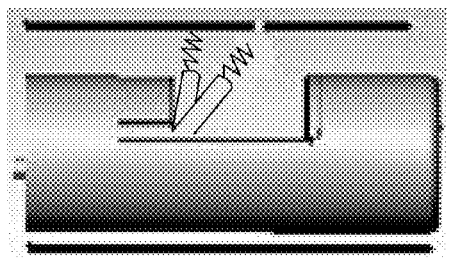

FIG. 9B—The sheaths 32 are pushed out of the channels 38 and the screws 30 are advanced and rotated until they penetrate and grab the tissue on opposite sides of the hole.

Figure 9C:
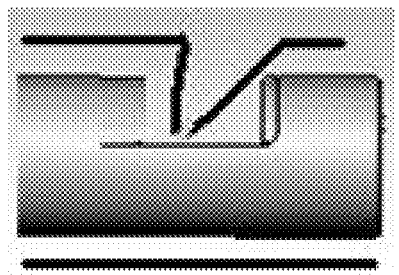

FIG. 9C—The sheaths 32 and the screws 30 with the tissue attached are pulled back into channels 38.

Figure 9D:
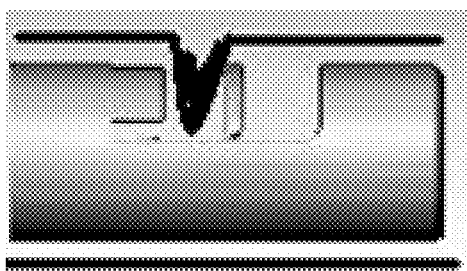

FIG. 9D—The cables attached to the legs 34 of the anvil 24 are pulled causing anvil 24 to move towards cartridge 26.

Figure 9E:
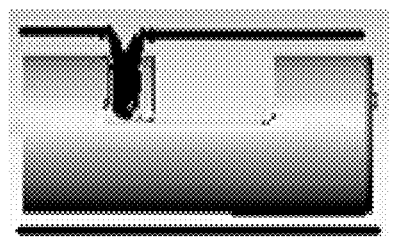

FIG. 9E—The tissue is compressed between the faces of the anvil 24 and the cartridge 26 and moveable cartridge section $26_2$ begins to slide into fixed cartridge section $26_1$. The legs of staples 44 begin to exit the slots 28, penetrate the layers of tissue and curl in the depressions 36.

Figure 9F:
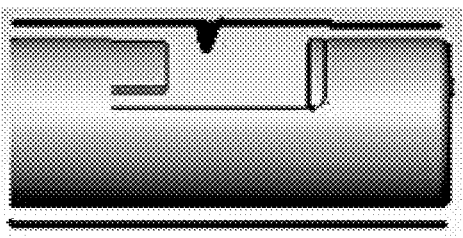

FIG. 9F—The stapling has been completed, screws 30 have been rotated to release their grip on the tissue, the cables attached to legs 34 have been released, and springs 42 have pushed the anvil 24 back to its original position, thereby freeing the stapled tissue. The closed hole is now inspected using the side viewing camera 16 and the endoscope can be withdrawn. If the hole is a large one, another endoscope containing a stapler of the invention can be introduced to the site of the hole and the same procedure followed again to apply a second array of staples next to the first array.

Figure 10:
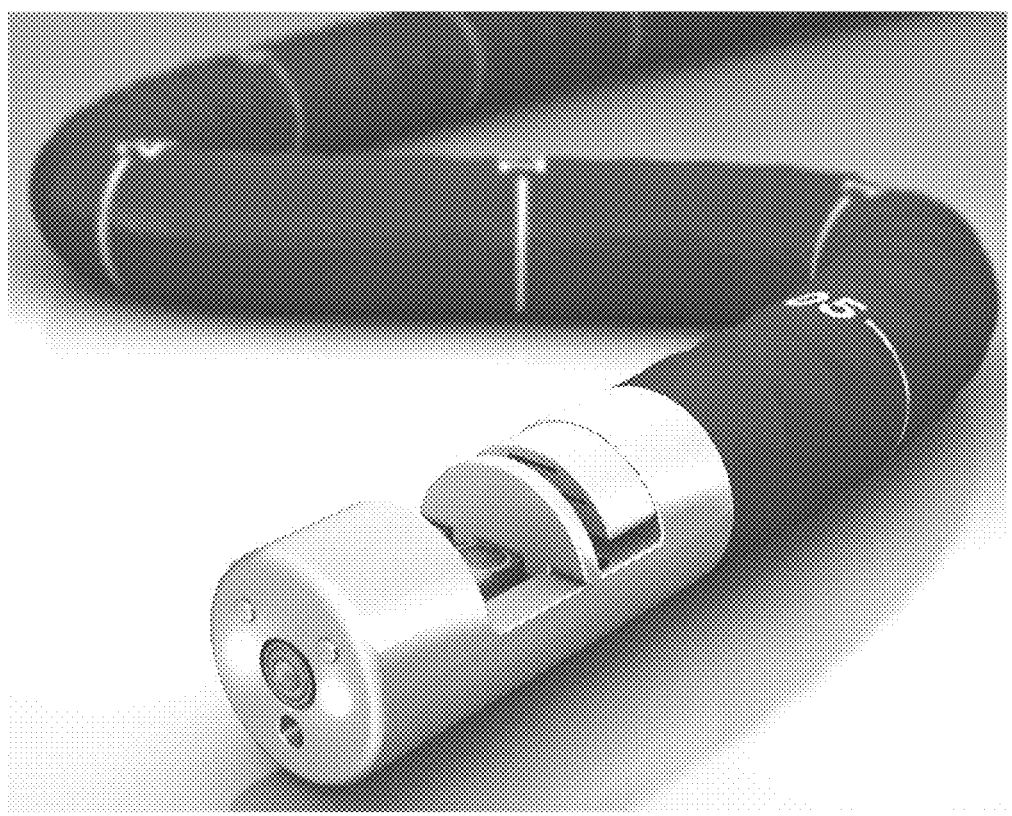
FIG. 10 shows the anvil in the approximate position it would be for ejecting the staples from the face of the cartridge.

FIG. 10 shows the anvil in the approximate position it would be for ejecting the staples from the face of the cartridge.

FIG. 11 to FIG. 13 show the front fastening embodiment of the stapler of the invention in the open and closed configurations. Most of the components of the stapler according to this embodiment are the same as for the side fastening embodiment mutatis mutandis and will not be further described. The only difference between the two embodiments being that in the front fastening embodiment a mechanism activated from the operating handle of the endoscope, e.g. a spring loaded cam system, must be provided to raise and lower the anvil to enable the tissue to be grabbed and pulled between the faces of the anvil and the cartridge for stapling.

Figures 14A, 14B, 14C:
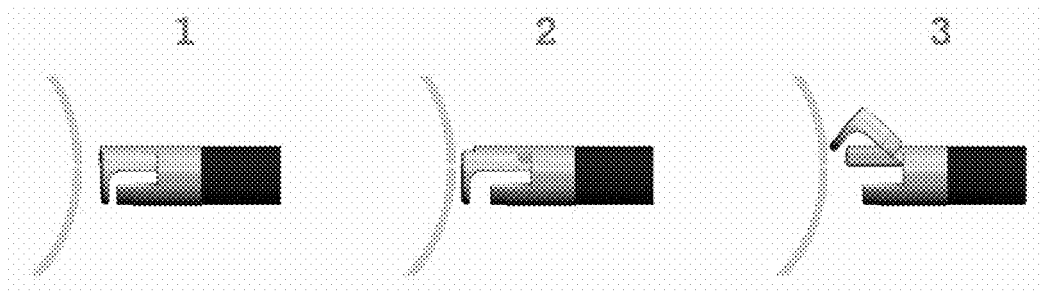
FIGS. 14A to 14F schematically show different stages in the operation of the front fastening embodiment of the stapler to close a hole in biological tissue.

FIGS. 14A to 14F schematically show different stages in the operation of the front fastening embodiment of the stapler to close a hole in biological tissue. The procedure is as follows:

FIG. 14A—With the anvil lowered, the endoscope is inserted into the body cavity using the camera 16 on the distal face 14 for visualization. The endoscope is advanced and steered until the hole in the tissue is viewed directly in front of the camera.

Figures 14D, 14E, 14F:
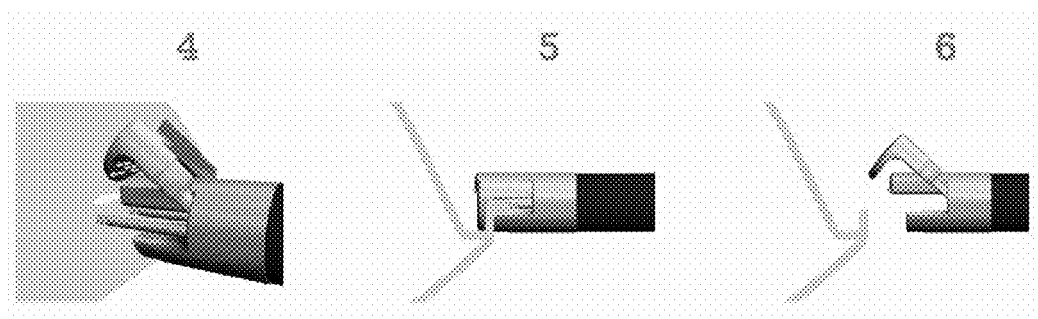

FIG. 14B—the mechanism is activated from the control handle of the endoscope causing the anvil to be pushed out of the distal end;

FIG. 14C—as the anvil continues to advance out of the end of the endoscope, it gradually opens;

FIG. 14D—The sheaths 32 are pushed out of the channels 38 and the screws 30 are advanced and rotated until they penetrate and grab the tissue on opposite sides of the hole.

FIG. 14E—The sheaths 32 and the screws 30 with the tissue attached are pulled back into channels 38, the anvil is pulled distally towards the face of the cartridge forcing the anvil down into its lowered position, the tissue is compressed between the faces of the anvil 24 and the face of cartridge 26, moveable cartridge section $26_2$ begins to slide into fixed cartridge section $26_1$, the legs of staples 44 begin to exit the slots 28 penetrate the layers of tissue and curl in the depressions 36.

FIG. 14F—The stapling has been completed, screws 30 have been rotated to release their grip on the tissue, the anvil 24 is returned to its open position, thereby freeing the stapled tissue. The closed hole is now inspected using the camera 16 and the endoscope can be withdrawn. If the hole is a large one, another endoscope containing a stapler of the invention can be introduced to the site of the hole and the same procedure followed again to apply a second array of staples next to the first array.

Figure 15:
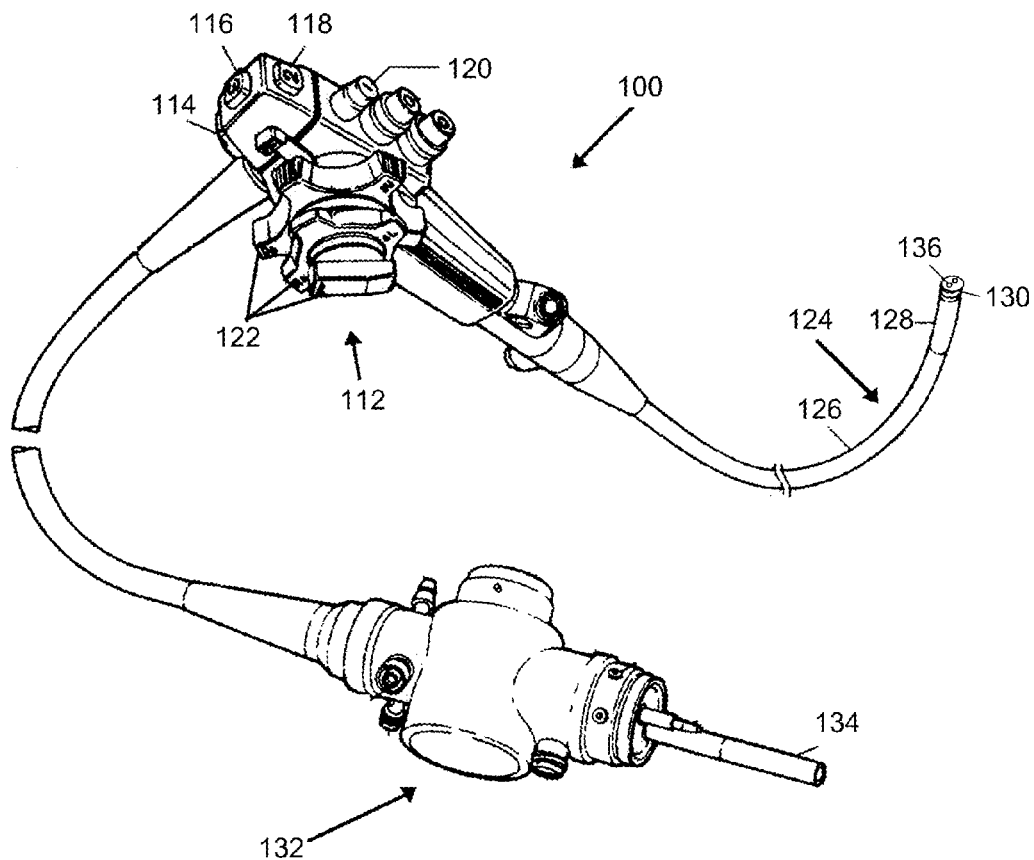
FIG. 15 schematically illustrates a conventional endoscope.

A conventional endoscope is illustrated in FIG. 15. Briefly the endoscope generally indicated at 100, is provided with a control section 112 (referred to as the "handle", "control handle", "operating handle") provided with suction valves, operating switches, articulation lock, etc., switches 114-120 being marked for illustrative purposes. Control wheels 122 are used for implementing the bending of the articulation section, locking the articulation section, activating accessories such as a stapler, etc. The endoscope 100 also comprises a connector section 132, which is used to connect air and water lines, light guides, etc, to the endoscope. The light guide is indicated at 134, for illustration purposes. The insertion tube 124 consists of three separate sections: a flexible portion 126, an articulation section 128 and a distal tip section 130. On the face of distal section 130 can be seen the distal ends of two working channels 136.

Although embodiments of the invention have been described by way of specific illustration, i.e. embodiments of an endoscopic surgical stapler for closing holes in tissue, it is anticipated by the inventors that the invention may be carried out by skilled persons with many variations, modifications, and adaptations, without exceeding the scope of the claims.

The invention claimed is:

1. An endoscopic surgical stapler for stapling tissue within a body cavity, said stapler comprised of:
   (a) an endoscopic device comprising an insertion section ending in a distal tip;
   (b) a stapler comprising:
      i) an anvil comprising a proximal face;
      ii) a staple cartridge containing an array of staples, said cartridge comprised of two portions: a fixed proximal portion and a moveable distal portion, said distal portion being adapted to be able to slide into said fixed portion when a force, pushing it in a proximal direction, is applied to a distal face of said distal portion, wherein said fixed proximal portion comprises a non-moveable backstop; and
      iii) moving means comprising cables for moving said anvil proximally and springs for moving said anvil distally in a direction parallel to an imaginary axis passing through said distal face of said distal portion of staple cartridge and said face of said anvil;
      wherein, when said moving means are activated causing said anvil to push against said moveable distal portion of said cartridge causing said moveable distal portion to slide into said fixed proximal portion of said cartridge, said non-moveable backstop prevents staples stored in said moveable distal portion of said cartridge from moving in a proximal direction and therefore the legs of said staples are passively forced to exit said distal portion of said cartridge through slots in said distal face of said moveable distal portion of said cartridge;
   (c) tissue grasping means which can be advanced out of and retracted into channels that travel through said insertion section and exit said distal tip at a location between the proximal face of the anvil and the distal face of the cartridge; and
   (d) one or more visualization means enabling observation of the operating site and inspection of the results of the stapling procedure.

2. The endoscopic surgical stapler according to claim 1, wherein the backstop comprises either staple pushers or internal slots.

3. The endoscopic surgical stapler according to claim 1, wherein the anvil, the cartridge, and the grasping means are located in a recess cut into a side of the distal tip.

4. The endoscopic surgical stapler according to claim 1, wherein the anvil, the cartridge, and the grasping means are located on the front of the distal tip.

5. The endoscopic surgical stapler according to claim 1, wherein the insertion section comprises one of the following:
   (a) a flexible section followed by an articulation section;
   (b) a semi rigid section;
   (c) a semi rigid section followed by an articulation section.

6. The endoscopic surgical stapler according to claim 1, wherein some or all of the components of said device are sterilizable and reusable.

7. The endoscopic surgical stapler according to claim 1, wherein all components of said device are discarded after a single procedure.

8. The endoscopic surgical stapler according to claim 1, wherein the visualization means are chosen from:
   (a) a miniature CCD camera;
   (b) a miniature CMOS camera;

(c) an objective lens optically coupled to proximally located processing and display means; and
(d) a bundle of imaging fibers.

9. The endoscopic surgical stapler according to claim 1, wherein the tissue grasping means are selected from:
(a) screws comprised of stiff wire bent into a spiral; or
(b) forceps.

10. A method for operating the endoscopic surgical stapler of claim 1 to staple tissue within a body cavity comprising:
(a) insert the endoscope into said body cavity;
(b) use the visualization means to see when the tissue to be stapled is viewed in the correct position relative to the grasping means;
(c) use said grasping means to grab the edges of the tissue to be stapled together;
(d) pull said grasping means with said tissue attached back into the channels;
(e) activate the means for moving said anvil causing said anvil to move towards the front face of the cartridge until said grabbed tissue is compressed between the faces of said anvil and said cartridge, whereupon, upon further motion of said anvil towards said cartridge, the legs of the staples begin to exit the slots, to penetrate the layers of said grabbed tissue and curl in the depressions;
(f) activate said grasping means to release their grip on said tissue;
(g) activate said anvil moving means causing said anvil to move back to its original position, thereby freeing the stapled tissue;
(h) inspect the stapled tissue using said visualization means;
(i) withdraw said endoscopic device from said body cavity.

11. The method according to claim 10, wherein the tissue contains a hole which is closed by stapling.

12. The method according to claim 11 wherein the hole in the tissue is large and said large hole is closed by repeating the method of claim 10 sequentially using one or more endoscopic surgical staplers of claim 1 to apply two or more arrays of staples next to each other until said large hole is completely closed.

13. The method according to claim 10, wherein the endoscopic surgical stapler of claim 1 is inserted into the body cavity through a working channel of a standard endoscope.

14. The method according to claim 13, wherein the visualization means are located on the standard endoscope and the stapler, without a camera and illumination fibers, is mounted on a flexible shaft that is inserted through a working channel of said endoscope.

* * * * *